US009120734B2

(12) United States Patent
Kelkar et al.

(10) Patent No.: US 9,120,734 B2
(45) Date of Patent: Sep. 1, 2015

(54) TWO-STEP SYSTEM AND METHOD FOR THE PRODUCTION OF METHYL ISOBUTYL KETONE

(71) Applicant: ClearWaterBay Technology, Inc., Pomona, CA (US)

(72) Inventors: Vaibhav V. Kelkar, Chino Hills, CA (US); Drow Lionel O'Young, Walnut, CA (US); Christianto Wibowo, Chino Hills, CA (US); Madhura Kelkar, Chino Hills, CA (US); Hok Chung Chan, Hong Kong (CN)

(73) Assignee: ClearWaterBay Technology, Inc., Pomona, CA (US)

( * ) Notice: Subject to any disclaimer, the term of this patent is extended or adjusted under 35 U.S.C. 154(b) by 0 days.

(21) Appl. No.: 14/289,592

(22) Filed: May 28, 2014

(65) Prior Publication Data

US 2015/0025277 A1    Jan. 22, 2015

Related U.S. Application Data

(60) Provisional application No. 61/847,507, filed on Jul. 17, 2013.

(51) Int. Cl.
  *C07C 45/73* (2006.01)
  *B01J 8/00* (2006.01)
  *B01J 19/00* (2006.01)

(52) U.S. Cl.
  CPC ............. *C07C 45/73* (2013.01); *B01J 19/0046* (2013.01); *B01J 2219/00006* (2013.01); *B01J 2219/00306* (2013.01)

(58) Field of Classification Search
  CPC ........................ C07C 45/73; B01J 2219/00006
  USPC .......................................... 568/388, 392, 396
  See application file for complete search history.

(56) References Cited

U.S. PATENT DOCUMENTS

| 2,827,490 | A | 3/1958 | Martin |
| 3,953,517 | A | 4/1976 | Schmitt et al. |
| 5,149,881 | A | 9/1992 | Ushikubo et al. |
| 5,684,207 | A | 11/1997 | Chen et al. |
| 6,762,328 | B2 | 7/2004 | Saayman et al. |
| 7,671,239 | B2 | 3/2010 | Hahn et al. |
| 8,242,314 | B2 | 8/2012 | Hahn et al. |
| 2010/0317897 | A1 | 12/2010 | Sawrey |

OTHER PUBLICATIONS

S. Kudo, "Formation of Higher Molecular Weight Ketones from Acetone or Isopropanol," J. Chem. Soc. Japan Ind. Chem. Sec., 58 (1955), 785-787.
Uhde GmbH, "Uhde Technology Profile, Methyl isobutyl ketone (MIBK)", 2 pages, 2005.
International Search Report and Written Opinion in International Application No. PCT/US2014/047086, mailed Oct. 8, 2014.

*Primary Examiner* — Sikarl Witherspoon
(74) *Attorney, Agent, or Firm* — Nixon Peabody LLP

(57) ABSTRACT

Embodiments of the present invention describe systems and methods for production of methyl isobutyl ketone (MIBK) from acetone and hydrogen in a two-step process. In a first step, acetone is converted to a product stream containing mesityl oxide (MO) at a temperature in the range of about 0-120° C. and a pressure in the range of about 1-3 atm. The composition of the product stream from the first reaction step is adjusted so that the resulting stream can undergo a favorable liquid-liquid separation in a decanter, and an MO rich product stream can be recovered. The composition of the feed to the decanter is controlled by choosing the number of reactor stages for the first reaction step and their operating temperatures, and/or by recycling some MIBK to the decanter feed. The method does not require a substantially complete conversion of acetone in the first reaction step, nor does it require a removal of DAA from the product of the first reaction step by separation.

15 Claims, 2 Drawing Sheets

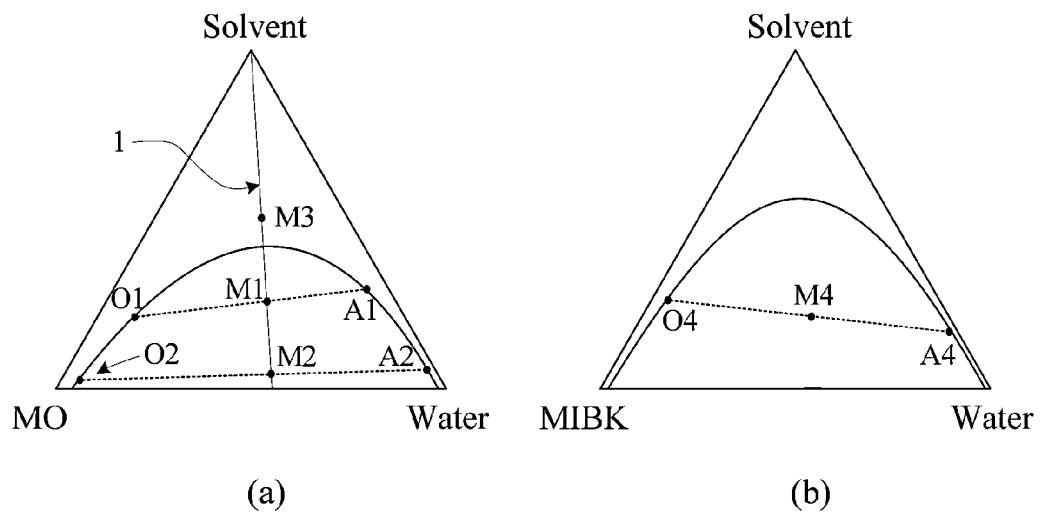
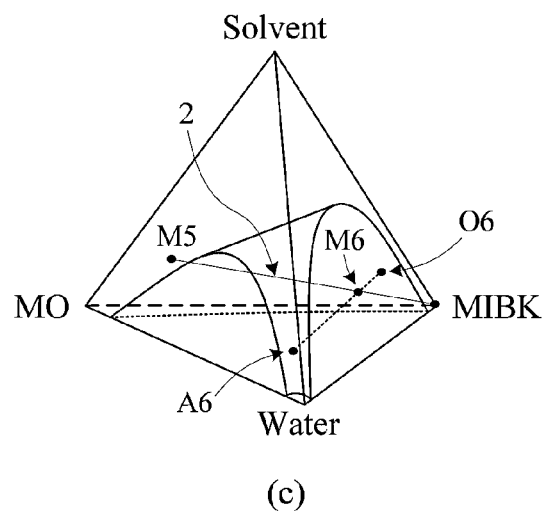
FIG. 1(a) - FIG. 1(c)
(not to scale)

TWO-STEP SYSTEM AND METHOD FOR THE PRODUCTION OF METHYL ISOBUTYL KETONE

RELATED APPLICATIONS

The present application claims the benefit of, and priority to, U.S. Provisional Patent Application Ser. No. 61/847,507, filed on Jul. 17, 2013, entitled "Two-Step System And Method For The Production Of Methyl Isobutyl Ketone", which is hereby incorporated by reference in its entirety.

FIELD OF THE INVENTION

The present invention relates to the production of Methyl isobutyl ketone (MIBK) from acetone and hydrogen. More specifically, the present invention relates to a method and system for production of MIBK in a two-step reaction process; the first reaction step performs aldol condensation and dehydration while the second reaction step performs hydrogenation.

BACKGROUND

Methyl isobutyl ketone (MIBK) is a colorless organic compound with the formula $(CH_3)_2CHCH_2C(O)CH_3$, which is widely used as an industrial solvent for nitrocellulose, lacquers, and certain polymers and resins. Another major use is as a precursor to N-(1,3-dimethylbutyl)-N'-phenyl-p-phenylene diamine (6PPD), an antiozonant used in tires.

Methods for producing MIBK are well known in the prior art. One such method involves manufacturing of MIBK from acetone via a three-step process (Kudo, S. "Formation of Higher Molecular Weight Ketones from Acetone or Isopropanol," *J. Chem. Soc. Japan Ind. Chem. Sec.*, 58 (1955), 785-787). Firstly, acetone undergoes a liquid phase aldol condensation reaction at low temperature in the presence of a basic catalyst to give diacetone alcohol (DAA). DAA is then dehydrated to give mesityl oxide (MO) with an acid catalyst at atmospheric pressure. Finally, MO is dehydrogenated to give MIBK. The three-step process is disadvantageous because of high initial investment, the need for cooling equipment for acetone condensation to DAA, and acid contamination due to the use of a homogeneous acid catalyst.

More recently, one-step processes combining the three steps into one have also been disclosed. U.S. Pat. No. 3,953,517 (assigned to Veba-Chemie Aktiengesellschaft, Germany) describes a method for producing MIBK by contacting acetone and hydrogen in the presence of a cation exchange catalyst containing a noble metal, at a temperature of about 50-200° C. and a pressure between 60 and 100 atmospheres. U.S. Pat. No. 5,149,881 (assigned to Mitsubishi Kasei Corporation, Japan) describes a similar method with palladium and a metal oxide and/or metal hydroxide treated with an organosilicon compound as the catalyst. U.S. Pat. No. 5,684,207 (assigned to Industrial Technology Research Institute, Taiwan) describes a one-step process including reacting acetone and hydrogen in the vapor/liquid phase at a temperature of about 100-300° C. and a pressure of about 100 to 1000 psig, in the presence of a modified ZSM-5 catalyst. Most commercial one-step MIBK processes these days employ a palladium-doped cation exchange resin, such as the Sasol process exclusively licensed by Uhde GmbH, Germany (Uhde GmbH, "Uhde Technology Profile: MIBK" (2005)). The major drawback of such one-step processes is the need for operation at an elevated pressure to keep the hydrogen in the liquid phase. Furthermore, the multifunctional catalyst that can effect condensation, dehydration, and hydrogenation reactions is typically expensive, and numerous byproducts may form as a result of combining the three chemical transformation steps in one reactor.

The use of two different catalysts for the production of MIBK from acetone has also been suggested. U.S. Pat. No. 6,762,328 (Catalytic Distillation Technologies, Pasadena, Tex.) ("the '328 patent") discloses a process which involves two reaction zones. The first zone is a catalytic distillation zone where acetone is reacted over an acidic ion exchange resin catalyst to form a product stream containing MO, water, and optionally, DAA, other by-products, and unreacted acetone. A product stream containing MO and water is recovered from this mixture, and separated into two liquid phases in a decanter. The MO rich organic stream is sent to the second reaction zone where it is reacted with hydrogen to form MIBK in the presence of a hydrogenation catalyst such as Ni on Al, Pd on Al, or Pd on C catalyst.

This process also suffers from disadvantages. When the product stream from the first reaction zone includes DAA, other by-products, and unreacted acetone, such components are removed by distillation. This involves distilling acetone twice, and MO and water once, which are both energy intensive. In another embodiment described in the '328 patent, the first reaction zone is operated so that substantially all of the acetone is converted, and the product stream contains at most traces of acetone. To achieve such a high acetone conversion, the process requires high catalyst loading in the first reaction zone, which is disadvantageous from the catalyst cost point of view.

Moreover, the process disclosed by the '328 patent uses a catalytic distillation column operating at total reflux as the first reaction zone, operating at a temperature of 100-120° C. in the catalyst bed, a temperature of 120-150° C. in the column reboiler, and a pressure of 2-7 bar. A continuous energy supply is needed in the reboiler to keep the reaction mixture in a state of boiling. Moreover, it is known that higher temperatures, such as those used in the '328 patent, promote the formation of heavier condensation products.

It is desirable to have a process which operates at as mild conditions as possible. Moreover, in order to minimize the energy cost for operating the process, it is desirable to have a separation sequence in which evaporation of the desired product or recycled component is minimized. Further developments are needed.

SUMMARY

Accordingly, embodiments of the present invention provides an improved process for the production of methyl isobutyl ketone (MIBK). In some embodiments, a method of producing MIBK is provided, comprising: in a first reaction step, introducing acetone, where at least a portion of the acetone undergoes a condensation reaction to form diacetone alcohol (DAA), followed by a dehydration reaction that converts at least a portion of the DAA to mesityl oxide (MO), in the presence of a suitable catalyst, and at pressures in the range of 1-3 atm and temperatures in the range of 20-120° C.; controlling the composition of a product stream after the first reaction step such that a favorable liquid-liquid phase split can be obtained in a decanter, without reacting acetone substantially completely and without first removing DAA by separation; recovering from the decanter, an organic phase rich in MO, and an aqueous phase not containing a substantial concentration of valuable organic components; in a second reaction step, contacting the organic phase containing MO with hydrogen, where MO is converted to MIBK in the presence of a suitable hydrogenation catalyst; and purifying the MIBK-rich stream from the second reaction step to produce high purity MIBK. In some embodiments the first reaction step is carried out in more than one reactor stages, with the last reactor stage operated such that a substantial portion in the range of more than 50% of the DAA formed in the prior reactor stages is converted back to acetone. The outlet of the first reaction step may be fed to a separator to remove a substantial portion of more than 90% (preferably more than 95%) of acetone, so as to produce a product stream rich in MO and with a low concentration of acetone and DAA, the low concentration of acetone being in the range of less than 1% by weight (preferably less than 0.5% by weight), and the low concentration of DAA being in the range of less than 5% by weight.

In other embodiments, the first reaction step is carried out in a single reactor stage, such that the product stream from the first reaction step contains a substantial concentration of DAA of more than 5% by weight. In some embodiments the outlet of the first reaction step is fed to a separator to remove a substantial portion of acetone in the range of more than 90% (preferably more than 95%), so as to produce a product stream rich in MO, and which has a low concentration of acetone, the low concentration of acetone being in the range of less than 1% by weight (preferably less than 0.5% be weight). The product stream may have a substantial concentration of DAA of more than 10% by weight. In some embodiments, an MIBK rich stream is added to the MO rich product stream, so as to produce a product stream with a low concentration of DAA, the low concentration of DAA being in the range of less than 5% by weight.

In some embodiments, the condensation reaction and dehydration reaction occur substantially simultaneously in the first reaction step.

In another aspect, embodiments of the present invention provide a system for producing methyl isobutyl ketone from acetone and hydrogen, comprising: a first reactor, said first reactor configured to receive acetone, where at least a portion of the acetone undergoes a condensation reaction to form DAA, followed by a dehydration reaction that converts at least a portion of the DAA to MO, in the presence of a suitable catalyst; a first separator, said first separator configured to control the composition of the outlet of the first reactor such that a favorable liquid-liquid phase split occurs, producing two liquid phases that can be subsequently separated in a decanter; a second reactor, said second reactor configured to contact the organic phase containing MO with hydrogen, where MO is converted to MIBK in the presence of a suitable hydrogenation catalyst; and a second separator, said second separator configured to purify the MIBK-rich stream from the second reactor to produce high purity MIBK. In some embodiments the first reactor is comprised of multiple reactor stages, and where the last reactor stage is configured such that a substantial portion of the DAA in the range of more than 50% formed in the prior reactor stages is converted back to acetone.

BRIEF DESCRIPTION OF THE DRAWINGS

Other aspects, embodiments and advantages of the invention will become apparent upon reading of the detailed description of the invention and the appended claims provided below, and upon reference to the drawings in which:

FIG. 1(a) shows a phase equilibrium diagram for a ternary system of mesityl oxide, water, and solvent, where the solvent is a mixture of acetone and diacetone alcohol;

FIG. 1(b) shows a phase equilibrium diagram for a ternary system of methyl isobutyl ketone, water, and solvent, where the solvent is a mixture of acetone and diacetone alcohol;

FIG. 1(c) shows a phase equilibrium diagram for a quaternary system of mesityl oxide, water, solvent, and methyl isobutyl ketone, where the solvent is a mixture of acetone and diacetone alcohol.

DETAILED DESCRIPTION

Figure 2:
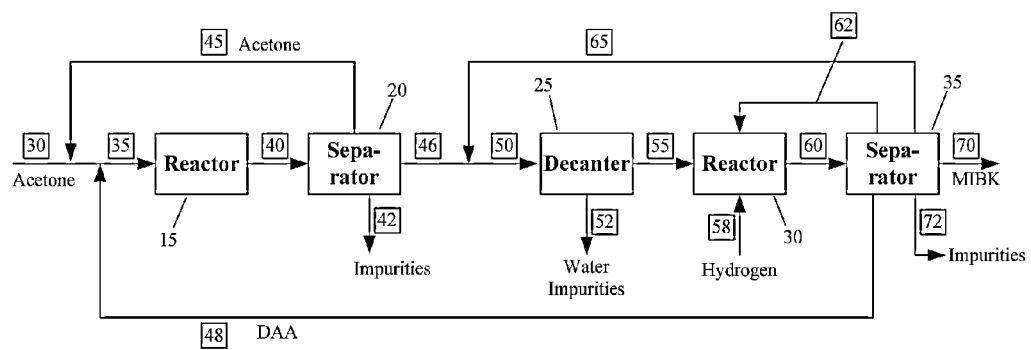
FIG. 2 shows a simplified flow diagram of a system and method for producing methyl isobutyl ketone from acetone according to some embodiments of the present the invention.

The present invention relates broadly to the production of methyl isobutyl ketone (MIBK) from acetone and hydrogen, and in particular to a two-step reaction system and method wherein a first reaction step performs aldol condensation and dehydration, and a second reaction step performs hydrogenation to form MIBK.

In some embodiments, in the first reaction step, acetone is converted to mesityl oxide (MO) via aldol condensation and dehydration reactions which are conducted simultaneously in the presence of a catalyst. More particularly, the catalyst may be an ion exchange resin catalyst such as an Amberlyst (trademark) resin, a zeolite, or any other suitable catalyst. The main reactions occurring in the first reaction step can be written as:

$$2\,\text{Acetone} \leftrightarrow \text{DAA} \tag{1}$$

$$\text{DAA} \rightarrow \text{MO} + \text{H}_2\text{O} \tag{2}$$

The aldol condensation of acetone is known to be limited by equilibrium. The equilibrium conversion of acetone to diacetone alcohol (DAA) is known to be around 23% at 0° C. and around 4% at 55° C. The simultaneous dehydration of DAA to MO shifts the equilibrium of reaction (1) to the right, and enables higher per pass conversions of acetone to DAA. The first reaction step may be carried out in a single reactor stage, or in multiple reactor stages, such as by using a cascade of two of more connected reactors, operating at relatively similar, or different conditions. The reactor(s) can be of any suitable type known in the art, and can be operated with the catalyst in suspension, such as in a stirred slurry reactor, or more typically, with the catalyst packed in a column. Apart from the reactions listed above there may also be side reactions which produce impurities such as triacetone alcohol (TAA), trimethylbenzene (TMB), phorone, isophorone, and other byproducts, so that the outlet stream from the first reaction step contains unreacted acetone, DAA, MO, water, and the impurities. The proportion of these components in the outlet stream depends on the operating conditions such as temperature and pressure used in the first reaction step. Higher temperatures promote the formation of heavier condensation products, hence mild conditions are preferred. However, the temperature of the first reaction step may be chosen in view of the reaction rate required to give reasonable per pass conversions using economically feasible catalyst amount. Also, the reaction temperature is related to the pressure, by vapor-liquid equilibrium. Accordingly, in some embodiments the first reaction step may be operated at a temperature in the range of about 20° C. to 120° C., and a pressure in the range of about 1 atm to 3 atm. If the first reaction step is carried out using more than one reactor stage, the operating conditions of each stage may be relatively similar, or preferably, they may be different, to better regulate the composition of the product stream.

The composition of the outlet of the first reaction step is controlled such that a favorable liquid-liquid phase split occurs, producing an aqueous and an organic liquid phase that are subsequently separated in a decanter. This is achieved by choosing the operating conditions for the first reaction step and/or by other means such as selectively adding or removing components. These means are described in more detail below.

In the second reaction step, the organic phase containing MO is contacted with hydrogen to form MIBK in the presence of a catalyst. More particularly, the catalyst may be any suitable hydrogenation catalyst such as nickel or palladium-doped alumina or carbon. The main reaction occurring in the second reaction step is:

$$MO + H_2 \rightarrow MIBK \quad (3)$$

There may also be side reactions which produce impurities such as methyl isobutyl carbinol (MIBC), diisobutyl ketone (DIBK), and other byproducts, so that the outlet stream from the second reaction step contains unreacted MO, hydrogen, MIBK, DAA, water and impurities.

Compared to the single-step process known in the prior art, the fact that the method of the present invention taught herein has a separate hydrogenation step provides advantages, such as for example that operation at high pressure is not necessary for the first reaction step, since there is no need for dissolving hydrogen into the liquid phase. Furthermore, side reactions such as hydrogenation of acetone to isopropanol can be avoided, thus improving the overall selectivity to MIBK. The need for a relatively expensive multifunctional catalyst to perform all three reactions in a single reactor can be eliminated. Moreover, compared to the three-step process known in the prior art, the method of the current invention features a more compact process and avoids potential problems with having a separate catalyst for the dehydration reaction, such as acid contamination of the final MIBK product.

As explained above, the outlet stream from the first reaction step contains unreacted acetone, DAA, MO, water, and impurities. Although the outlet stream from the first reaction step can be introduced directly to the second reaction step without any separation, it is preferable to recover MO as a substantially rich product stream from this mixture. This system of components exhibits a liquid-liquid phase split under certain conditions, where a liquid mixture with an appropriate composition can separate into two liquid phases in a decanter. This aspect of the present invention can be advantageously used to recover an MO rich stream from this mixture. However, in order to employ this separation method, the composition of the outlet stream from the first reaction step has to be manipulated such that it can split into two liquid phases. Moreover, in order to get an effective separation, such that the loss of valuable organic components to the aqueous phase is minimized, it is important to prepare the mixture composition of a particular kind.

A general description of the liquid-liquid phase equilibrium (LLE) behavior for this system is now described. The existence of a liquid-liquid phase split depends on the thermodynamic properties of the components in the mixture, as well as the temperature and pressure. The LLE behavior of a system can be represented on a phase diagram. For a three component system at a fixed temperature and pressure, the phase diagram takes the shape of a triangle, with the component compositions in weight fraction plotted on a triangular grid. The range of compositions under which a phase split is observed is defined by an enclosed region ('LLE envelope') within the plot.

FIG. 1(a) shows a sketch of a LLE phase diagram for a system comprising MO, water, and 'solvent' at a fixed pressure and temperature. The solvent may represent pure acetone, pure DAA, or a mixture of acetone and DAA, in any proportion ranging from 0% acetone to 0% DAA. Such a representation is possible since both acetone and DAA show a qualitatively similar LLE behavior in a mixture with MO and water. Pure MO and pure water are completely miscible with acetone and DAA; however, MO and water are not fully miscible with each other. Any composition of the mixture of MO, water, acetone and DAA is represented by a point within the triangle shown in the figure. It should be understood by those of ordinary skill in the art that the system may include other components or solutes such as impurities, unreacted reactants, isomers and the like; however, for purposes of the present invention we are concerned only with the primary components in the solution—MO, acetone, DAA, and water.

The shaded area represents the LLE envelope in which liquid-liquid phase split will occur. Any composition outside this region is completely miscible and forms a single phase. Any composition within this region forms two liquid phases—a water rich aqueous phase, and a MO rich organic phase. The compositions of the two phases are shown by points where the 'tie-line' passing through the mixture composition meets the boundary of the LLE envelope. For example, the mixture composition denoted by point M1 in FIG. 1(a) will phase split in a decanter into an organic phase O1 and aqueous phase A1. If the mixture composition is outside the LLE envelope, such as point M3 in FIG. 1(a), some solvent may be removed from the mixture so that the mixture composition moves along line 1 in FIG. 1(a) towards point M1, to produce a suitable composition inside the LLE envelope. According to embodiments of the present invention, the size of the LLE envelope can be controlled by adjusting the concentration ratio of the two solvent components, in this case acetone and DAA, as well as the operating temperature of the decanter. Moreover, the position of the feed mixture within the LLE envelope can be controlled by adjusting the composition of the feed mixture.

For a particular solvent composition and decanter temperature, the liquid-liquid region is widest on the MO-water edge, i.e., when no acetone or DAA are present. With an increasing concentration of acetone or DAA, the liquid-liquid region becomes narrower, until it completely disappears. A narrower liquid-liquid region implies that the aqueous phase corresponding to a certain decanter feed will have a significant concentration of MO, acetone and DAA, and the corresponding organic phase will have a significant concentration of water. This is disadvantageous because it entails recovering the valuable organic components lost to the aqueous phase using additional operations such as distillation. Referring again to FIG. 1(a), a decanter feed corresponding to point M2 produces a cleaner liquid-liquid split as compared to a decanter feed corresponding to point M1. Thus for an effective or favorable liquid-liquid separation, it is important to prepare a decanter feed such that a substantially clean liquid-liquid split is achieved in the decanter, and the loss of valuable organic components, especially DAA, to the aqueous phase is minimized.

This can be achieved by operating the first reaction step at a high conversion of acetone and DAA, or by separating acetone and DAA from the product of the first reaction step. For example, U.S. Pat. No. 6,762,328 describes that when the product stream from the first reaction zone includes DAA, other by-products, and unreacted acetone, these are removed in a treatment zone. The treatment process described in the '328 patent involves subjecting the product from the first reaction zone to a series of distillation operations to remove acetone, DAA, and heavier impurities so as to give a decanter feed rich in MO. In another embodiment described in the '328 patent, the first reaction zone is operated so that substantially all of the acetone is converted, so that the product stream comprises substantially only MO, DAA and water, with at most traces of residual acetone. In a variation of the above embodiments, the '328 patent calls for additionally converting all the DAA to MO, using a zone of temperature and water resistant acid catalyst near the reboiler of the catalytic distillation unit of the first reaction zone. However, these methods are disadvantageous from the point of view of capital and/or energy cost.

According to the present invention, an understanding of the reaction and phase equilibrium of the system allows a distinct and significantly improved way to control the composition of the first reaction step so as to produce a favorable liquid-liquid separation in the decanter, without reacting acetone substantially completely in the first reaction step, and without separating DAA from the product mixture or outlet from the first reaction step.

According to one embodiment of the present invention, the first reaction step is carried out in at least two reactor stages. When two reactor stages are used, the first reactor stage is responsible for the majority of the conversion of acetone to DAA and MO. The temperature, pressure, and the catalyst volume provided in the first reactor stage are chosen in order to achieve a suitable per pass conversion of acetone, which need not be a substantially complete conversion, but may be any suitable conversion from about 10% to 100%. Higher temperatures promote the formation of heavier condensation byproducts, hence mild conditions are preferred. However, the temperature may be chosen so as to achieve the desired acetone conversion using an economically feasible volume of catalyst. Accordingly, the first reaction stage may be operated at a temperature in the range of about 20° C. to 120° C., preferably in a range of about 20° C. to 100° C., and a pressure in the range of about 1 atm to 3 atm. The proportion of acetone and DAA in the outlet of the first reactor stage depends on the temperature. At higher temperatures, the equilibrium of reaction (1) is shifted in the direction of more acetone and less DAA. The second reactor stage is provided to substantially reduce the proportion of DAA present in the outlet of the first reactor stage, by converting a large portion of the DAA back to acetone. Accordingly, the second reactor may operate at a temperature higher than the first reactor stage, within a range of about 20° C. to 120° C., preferably in a range of about 50° C. to 120° C. Note that the second reactor stage is not intended to convert DAA to MO, or to convert additional acetone to DAA. The catalyst used in the second reactor stage may be the same as that in the first reactor stage, or it may be a catalyst without the capability of catalyzing the dehydration of DAA to MO (reaction (2)), such as a basic ion exchange resin catalyst. The volume of catalyst provided in the second reactor stage is such that the desired reduction in the concentration of DAA can be attained, as dictated by reaction equilibrium. Preferably, it is a fraction of the catalyst volume used in the first reactor stage. If more than two reactor stages are used for the first reaction step, the temperature and catalyst amount in the final reactor stage is chosen so as to achieve the desired reduction in the DAA concentration.

The outlet stream from the last reactor stage in the first reaction step contains acetone, MO, water, residual DAA, and impurities. The composition of this stream is further adjusted by removing most of the acetone in a separator unit such as a distillation column. The acetone recovered in the overhead of the distillation column is recycled to the first reaction stage in the first reaction step. A small fraction containing heavier impurities may be withdrawn from the bottom of the distillation column. The remaining product stream containing mainly MO and water is withdrawn from a point at or near the bottom of the distillation column. This is then cooled and subjected to a liquid-liquid split in a decanter from which an MO rich organic phase and an aqueous phase are withdrawn. The organic phase is subjected to the second reaction step, as described earlier. The aqueous phase may be sent to a wastewater treatment facility, or subjected to further treatment if desired, to recover the small amount of MO and DAA contained within.

According to another embodiment of the present invention, the first reaction step may be operated with only one reactor stage, with the temperature, pressure, and catalyst volume chosen so as to achieve a suitable per pass conversion of acetone, which need not be a substantially complete conversion, but may be any suitable conversion from about 10% to 100%. The product stream from the first reaction step may contain a significant amount of DAA, along with unreacted acetone, MO, water, and impurities. This stream is first subjected to a distillation operation to remove most of the acetone, which is recycled to the first reaction step. A small fraction containing heavier impurities may be withdrawn from the bottom of the distillation column. The remaining product stream containing mainly MO and water is withdrawn from a point at or near the bottom of the distillation column. This stream may contain a significant concentration of DAA, and may cause a sloppy liquid-liquid separation if introduced to a decanter. To obtain a favorable liquid-liquid separation, the composition of this stream is adjusted by introducing another organic component into it. This component should be miscible with MO, acetone and DAA, but highly immiscible with water. Preferably, this component is MIBK. More preferably, the composition of the product stream containing MO is adjusted by mixing it with an MIBK rich stream from the downstream part of the process. The resulting stream has a composition that produces a favorable liquid-liquid split in a decanter, such that the loss of valuable organic components, especially DAA and MO, to the aqueous phase are minimized. This is explained by referring to the LLE phase diagrams shown in FIGS. 1(b) and 1(c).

FIG. 1(b) shows a liquid-liquid equilibrium phase diagram for the system comprising MIBK, water, and 'solvent'. The solvent may represent pure acetone, pure DAA, or a mixture of acetone and DAA, in any proportion ranging from 0% acetone to 0% DAA. The shaded area represents the LLE envelope in which liquid-liquid split will occur. Compared to the MO/water/solvent system represented in FIG. 1(a), the MIBK/water/solvent system exhibits a larger LLE envelope, with a cleaner split between the organic and aqueous phases. Moreover, the tie lines for the MIBK/water/solvent system are such that more of the solvent (i.e. acetone and DAA) present in the decanter feed is retained within the organic phase, and less goes to the aqueous phase. This is contrary to the MO/water/solvent system, where a larger proportion of the DAA and acetone present in the decanter feed, are lost to the aqueous phase. Thus, adding MIBK to the decanter feed has a favorable effect on the liquid-liquid separation process.

Referring specifically to FIG. 1(c), a sketch of the phase diagram of a quaternary system involving MO, water, solvent, and MIBK is shown. The shaded three-dimensional region represents the LLE envelope at a fixed temperature, in which liquid-liquid phase split will occur. According to the present invention, the size of the LLE envelope can be controlled by adjusting the concentration ratio of the two solvent components, in this case acetone and DAA, as well as the operating temperature of the decanter. Moreover, the position of the feed mixture within the LLE envelope can be controlled by adjusting the composition of the product mixture withdrawn from the acetone recovery column, and the amount of MIBK added to the product mixture.

If the composition of product mixture is located outside the LLE envelope, such as point M5 in FIG. 1(c) (point M5 is located on the triangular face of the tetrahedron, with MO, water, and solvent as vertices), MIBK may be added to the mixture so that the mixture composition moves along line 2 in FIG. 1(c) towards point M6 (located in the interior of the tetrahedron), to produce a suitable composition inside the LLE envelope. The composition of point M6 in FIG. 1(c) will split to give an organic stream O6 and an aqueous stream A6 in the decanter.

One exemplary embodiment of a system and method of the present invention is illustrated in FIG. 2. In general, the system 10 is comprised of a condensation and dehydration reactor unit 15; a separator unit 20 for removing unreacted acetone and optionally, heavy impurities; a decanter 25 for separating the aqueous phase from the organic phase; a hydrogenation reactor unit 30; and a separator unit 35 for recovering high purity MIBK. Fresh acetone feed 30 is mixed with recycled acetone and DAA, and conveyed to reactor 15 where it is contacted with a suitable catalyst such that a part of the acetone is converted to MO via reactions (1) and (2). Reactor 15 may be comprised of one or more reactor stages. The outlet stream 40 contains unreacted acetone, DAA, MO, water, and impurities generated from side reactions in reactor 15. Unreacted acetone is separated in a separator 20 using a suitable method such as distillation, and returned to the first reactor through line 45. Impurities such as TAA, TMB, phorone, and isophorone are also optionally separated and purged through line 42.

In one embodiment of the invention, the reactor 15 is comprised of more than one reactor stage, such as two reactor stages. The first reactor stage converts a part of the acetone to MO. The final reactor stage operates at a higher temperature, and is responsible for converting a significant portion of the DAA back to acetone. The resulting stream 46 lies within the LLE envelope, and preferably has a low concentration of acetone and DAA, such that a favorable liquid-liquid phase split occurs in a decanter 25.

In another embodiment of the invention, reactor 15 consists of one reactor stage only, and the stream 46 may contain a significant amount of DAA. In this case, stream 46 may be mixed with a recycle stream 65 containing mainly MIBK and water to produce a combined stream 50 with a composition within the LLE envelope, such that a favorable liquid-liquid split occurs in decanter 25.

In a third embodiment of the invention, the two embodiments described above may be combined.

In all cases, the aqueous phase 52 recovered in the decanter is preferably low in valuable organics, especially DAA and MO, and can be sent to a wastewater treatment facility, or can be optionally processed further to recover valuable organics. The organic phase 55 is preferably rich in MO, and is sent to a second reactor 30, where it is contacted with fresh hydrogen feed 58 and recycled hydrogen 62. The outlet stream 60 goes to a separator 35, in which pure MIBK is recovered through line 70 using a suitable method such as distillation. An MIBK rich stream 65 may be withdrawn from separator 35, and recycled to decanter 25. Unreacted hydrogen is returned to the second reactor 30 through line 62. Unreacted reactants such as DAA may be recovered in stream 48 and recycled to the first reactor 15. Impurities from the process are purged through line 72.

EXAMPLES

Simulated experiments are provided below to further illustrate embodiments of the system and method of the present invention. These simulated experiments are provided for illustration purposes only and are not intended to limit the scope of the invention in any way. Reference is made to the process block diagram shown in FIG. 2. Table 1 shows the stream compositions in wt % for major streams in the various examples. The focus of the examples 1-5 is on the reactor unit 15, the separator 20, and the decanter 25.

Example 1

Example 1 illustrates the need for the present invention. The first reaction step is carried out in a single reactor stage operating at 40° C. and 1 atm. Suitable amount of catalyst is provided to achieve a per pass acetone conversion of 54.6%. The outlet of the first reaction step is sent to a distillation column where acetone is removed as an overhead product. The MO rich stream recovered from the bottom of the column is cooled and sent to the decanter, where it splits into an aqueous and organic phase. The decanter feed has about 5% DAA, leading to a relatively sloppy liquid-liquid split, with a significant amount of DAA lost to the aqueous phase. The DAA concentration in the aqueous phase is 5.9%.

Example 2

Example 2 is also intended show the need for the present invention. The process flow and is identical to that in Example 1. The single reactor stage used for the first reaction step operates at the same conditions as in Example 1, but has a smaller amount of catalyst, leading to a per pass conversion of 30.5%. The DAA concentration in the reactor outlet as well as in the decanter feed are higher than in Example 1. The loss of DAA to the aqueous phase is significantly higher, with an aqueous phase DAA concentration of 20.6%

Example 3

Example 3 illustrates one embodiment of the present invention. The first reaction step is carried out in two reactor stages. The first reactor stage operates at 40° C. and 1 atm. Suitable amount of catalyst is provided to achieve a per pass acetone conversion of about 54%, which is similar to that in Example 1. An additional, or second reactor stage, is provided in this embodiment of the present invention. The second reactor stage is operated at 100° C. and 1 atm, and is provided with just enough catalyst to convert a significant amount of DAA back to acetone, as directed by the changed reaction equilibrium at the higher temperature. The rest of the process flow is similar to that described in Example 1. Due to the conversion of DAA back to acetone in the second reactor stage, the feed to the decanter is lean in DAA. The resulting loss of DAA to the aqueous phase is greatly diminished, with an aqueous phase DAA concentration of only 0.6%. This example is contrasted with Example 1 which operates at a similar acetone conversion, and illustrates the benefit of the present invention. An MO rich organic phase can be recovered by a liquid-liquid phase split after the first reaction step, with minimal loss of valuable organics to the aqueous phase, without having to react acetone substantially completely, and without first removing DAA by separation.

Example 4

Example 4 uses a process flow and operating conditions identical to that in Example 3, with the first reaction step operated with two reactor stages. The per pass acetone conversion is about 28%, which is similar to that in Example 2.

However, in contrast to Example 2, the second reactor stage provided in Example 4 reduces the DAA concentration in the decanter feed. The corresponding loss of DAA to the aqueous phase is greatly diminished, with an aqueous phase DAA concentration of only 0.7%. This is in contrast with the large loss of DAA in Example 2. Example 4 illustrates that the method of the present invention can be applied even with a low per pass acetone conversion in the first reaction step.

Example 5

Example 5 illustrates a second embodiment of the present invention. The first reaction step operates with only one reactor stage, as in Example 2. After removing acetone in a distillation column, the product contains a significant concentration of DAA (18 wt %). This composition is adjusted by mixing an MIBK rich recycle stream from the downstream process. The resulting product stream is introduced to a decanter where, due to the presence of MIBK, the valuable organic components are retained in the organic phase. The loss of DAA to the aqueous phase is much lower than in Example 2. Again, this example illustrates a simple process to recover an MO rich organic phase after the first reaction step, with a minimal loss of valuable organics to the aqueous phase, without having to react acetone substantially completely, and without first removing DAA by separation.

TABLE 1

| Component | Stream 35 Feed to reaction step 1 | Stream 40a Outlet of reactor stage 1 | Stream 40b Outlet of reactor stage 2 | Stream 46 After acetone removal | Stream 65 MIBK recycle | Stream 50 Decanter feed | Stream 55 Organic phase | Stream 52 Aqueous phase |
|---|---|---|---|---|---|---|---|---|
| Composition, weight% | | | | | | | | |
| Example 1 | | | | | | | | |
| ACETONE | 96.5% | 43.8% | — | 0.1% | — | 0.1% | 0.1% | 0.1% |
| DAA | 2.4% | 2.8% | — | 5.1% | — | 5.1% | 5.0% | 5.9% |
| MO | 0.2% | 43.6% | — | 78.6% | — | 78.6% | 87.5% | 3.3% |
| MIBK | 0.0% | 0.0% | — | 0.1% | — | 0.1% | 0.1% | 0.0% |
| WATER | 0.8% | 8.7% | — | 14.4% | — | 14.4% | 5.4% | 90.3% |
| IMPURITIES | 0.1% | 1.1% | — | 1.7% | — | 1.7% | 1.9% | 0.4% |
| TOTAL | 100.0% | 100.0% | — | 100.0% | — | 100.0% | 100.0% | 100.0% |
| Example 2 | | | | | | | | |
| ACETONE | 93.3% | 64.9% | — | 0.2% | — | 0.2% | 0.2% | 0.2% |
| DAA | 5.4% | 6.1% | — | 18.0% | — | 18.0% | 17.7% | 20.6% |
| MO | 0.1% | 22.8% | — | 66.8% | — | 66.8% | 73.2% | 3.5% |
| MIBK | 0.0% | 0.0% | — | 0.1% | — | 0.1% | 0.1% | 0.0% |
| WATER | 1.1% | 5.3% | — | 12.2% | — | 12.2% | 5.8% | 75.1% |
| IMPURITIES | 0.1% | 0.9% | — | 2.7% | — | 2.7% | 3.0% | 0.6% |
| TOTAL | 100.0% | 100.0% | — | 100.0% | — | 100.0% | 100.0% | 100.0% |
| Example 3 | | | | | | | | |
| ACETONE | 98.7% | 44.0% | — | 0.1% | — | 0.1% | 0.1% | 0.1% |
| DAA | 0.2% | 2.9% | — | 0.5% | — | 0.5% | 0.5% | 0.6% |
| MO | 0.2% | 43.3% | — | 82.4% | — | 82.4% | 91.9% | 3.3% |
| MIBK | 0.0% | 0.0% | — | 0.1% | — | 0.1% | 0.1% | 0.0% |
| WATER | 0.8% | 8.7% | — | 15.0% | — | 15.0% | 5.4% | 95.7% |
| IMPURITIES | 0.1% | 1.1% | — | 1.9% | — | 1.9% | 2.0% | 0.3% |
| TOTAL | 100.0% | 100.0% | — | 100.0% | — | 100.0% | 100.0% | 100.0% |
| Example 4 | | | | | | | | |
| ACETONE | 98.5% | 65.3% | 71.1% | 0.3% | — | 0.3% | 0.3% | 0.2% |
| DAA | 0.1% | 6.2% | 0.2% | 0.6% | — | 0.6% | 0.6% | 0.7% |
| MO | 0.1% | 22.3% | 22.4% | 80.9% | — | 80.9% | 89.7% | 3.3% |
| MIBK | 0.0% | 0.0% | 0.0% | 0.1% | — | 0.1% | 0.1% | 0.0% |
| WATER | 1.2% | 5.2% | 5.3% | 14.6% | — | 14.6% | 5.5% | 95.1% |
| IMPURITIES | 0.1% | 1.0% | 1.0% | 3.5% | — | 3.5% | 3.8% | 0.7% |
| TOTAL | 100.0% | 100.0% | 100.0% | 100.0% | — | 100.0% | 100.0% | 100.0% |
| Example 5 | | | | | | | | |
| ACETONE | 93.3% | 64.9% | — | 0.2% | 0.0% | 0.2% | 0.0% | 0.0% |
| DAA | 5.4% | 6.1% | — | 18.0% | 0.3% | 18.0% | 4.7% | 0.7% |
| MO | 0.1% | 22.8% | — | 66.8% | 0.2% | 66.8% | 17.4% | 0.1% |
| MIBK | 0.0% | 0.0% | — | 0.1% | 99.4% | 0.1% | 76.0% | 0.2% |
| WATER | 1.1% | 5.3% | — | 12.2% | 0.2% | 12.2% | 1.3% | 98.9% |
| IMPURITIES | 0.1% | 0.9% | — | 2.7% | 0.0% | 2.7% | 0.7% | 0.0% |
| TOTAL | 100.0% | 100.0% | — | 100.0% | 100.0% | 100.0% | 100.0% | 100.0% |

As illustrated above, embodiments of the present invention provide significantly improved systems and methods for the production of MIBK. The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

We claim:

1. A method for producing methyl isobutyl ketone (MIBK) from acetone and hydrogen, comprising:
    in a first reaction step, introducing acetone, where a portion of the acetone undergoes a condensation reaction to form diacetone alcohol (DAA), followed by a dehydration reaction that converts at least a portion of the DAA to mesityl oxide (MO), in the presence of a suitable catalyst;
    controlling the composition of the outlet of the first reaction step by removing acetone and adding an appropriate amount of MIBK such that a favorable liquid-liquid phase split occurs, producing two liquid phases that can be subsequently separated in a decanter without reacting acetone substantially completely and without first removing DAA by separation;
    in a second reaction step, contacting the organic phase containing MO with hydrogen, where MO is converted to MIBK in the presence of a suitable hydrogenation catalyst; and
    purifying the MIBK-rich stream from the second reaction step to produce high purity MIBK.

2. The method according to claim 1, where the condensation and dehydration reaction occurs at a temperature in the range of about 20-120° C. and a pressure in the range of about about 1-3 atm.

3. The method according to claim 1, where the first reaction step is carried out in more than one reactor stages, with the last reactor stage operated such that a substantial portion of the DAA formed in the prior reactor stages is converted back to acetone.

4. The method according to claim 3, where the outlet of the first reaction step is fed to a separator to remove a substantial portion of acetone, so as to produce a product stream rich in MO and with a low concentration of acetone and DAA.

5. The method according to claim 4, where the product stream containing MO is introduced to a decanter where it splits into two liquid phases, and where an MO rich organic phase is withdrawn from the decanter.

6. The method according to claim 1, where the first reaction step is carried out in a single reactor stage, such that the product stream from the first reaction step contains a substantial concentration of DAA.

7. The method according to claim 6, where the outlet of the first reaction step is fed to a separator to remove a substantial portion of acetone, so as to produce a product stream rich in MO, and which has a low concentration of acetone.

8. The method according to claim 7 where the product stream has a substantial concentration of DAA.

9. The method according to claim 7, where an MIBK rich stream is added to the MO rich product stream, so as to produce a product stream with a low concentration of DAA.

10. The method according to claim 9, where the product stream containing MO is introduced to a decanter where it splits into two liquid phases, and where an MO rich organic phase is withdrawn from the decanter.

11. A system for producing methyl isobutyl ketone (MIBK) from acetone and hydrogen, comprising:
    a first reactor, said first reactor configured to receive acetone and does not perform simultaneous separation of the acetone such as by distillation, where a portion of the acetone undergoes a condensation reaction to form diacetone alcohol (DAA), followed by a dehydration reaction that converts at least a portion of the DAA to mesityl oxide (MO), in the presence of a suitable catalyst;
    a first separator, said first separator configured to control the composition of the outlet of the first reactor by removing acetone and adding an appropriate amount of MIBK such that a favorable liquid-liquid phase split occurs, producing two liquid phases that can be subsequently separated in a decanter, without reacting acetone substantially completely and without first removing DAA by separation;
    a second reactor, said second reactor configured to contact the organic phase containing MO with hydrogen, where MO is converted to MIBK in the presence of a suitable hydrogenation catalyst; and
    a second separator, said second separator configured to purify the MIBK-rich stream from the second reactor to produce high purity MIBK.

12. The system according to claim 11 further comprising:
    a decanter, said decanter configured to separate the two liquid phases produced from the first separator into the organic phase and an aqueous phase.

13. The system according to claim 11 where the first reactor is comprised of one or more reactor stages.

14. The system according to claim 11 where the first reactor is comprised of multiple reactor stages, and where the last reactor stage is configured such that a substantial portion of the DAA formed in the prior reactor stages is converted back to acetone.

15. The system according to claim 12 where an MIBK rich stream recovered from the second separator is added to the decanter.

* * * * *